United States Patent [19]
Lopin et al.

[11] Patent Number: 5,800,462
[45] Date of Patent: Sep. 1, 1998

[54] ELECTROTHERAPY CIRCUIT FOR PRODUCING THERAPEUTIC DISCHARGE WAVEFORM BASED ON HIGH-CURRENT SENSING PULSE

[75] Inventors: Michael L. Lopin, Newton; Shervin Ayati, Sudbury, both of Mass.

[73] Assignee: ZMD Corporation, Wilmington, Del.

[21] Appl. No.: 769,045

[22] Filed: Dec. 18, 1996

[51] Int. Cl.⁶ .......................................... A61N 1/37
[52] U.S. Cl. ............................................ 607/7; 607/8
[58] Field of Search .......................... 607/5–8, 28, 4, 607/9, 11

[56] References Cited

U.S. PATENT DOCUMENTS

| | | |
|---|---|---|
| 3,860,009 | 1/1975 | Bell et al. |
| 4,576,170 | 3/1986 | Bradley et al. |
| 4,595,010 | 6/1986 | Radke |
| 4,637,397 | 1/1987 | Jones et al. |
| 4,768,512 | 9/1988 | Imran |
| 4,800,883 | 1/1989 | Winstrom |
| 4,821,723 | 4/1989 | Baker, Jr. et al. |
| 4,823,796 | 4/1989 | Benson |
| 4,998,531 | 3/1991 | Bocchi et al. |
| 5,083,562 | 1/1992 | de Coriolis et al. |
| 5,199,429 | 4/1993 | Kroll et al. |
| 5,215,081 | 6/1993 | Ostroff ........................... 607/8 |
| 5,230,336 | 7/1993 | Fain et al. ....................... 607/7 |
| 5,334,219 | 8/1994 | Kroll .............................. 607/5 |
| 5,350,403 | 9/1994 | Stroetmann et al. ............. 607/5 |
| 5,391,186 | 2/1995 | Kroll et al. ..................... 607/5 |
| 5,411,525 | 5/1995 | Swanson et al. ................. 607/5 |
| 5,413,591 | 5/1995 | Knoll ............................. 607/6 |
| 5,431,684 | 7/1995 | Archer et al. ................... 607/5 |
| 5,431,687 | 7/1995 | Kroll ............................. 607/8 |
| 5,441,521 | 8/1995 | Hedberg ......................... 607/6 |
| 5,507,781 | 4/1996 | Kroll et al. ..................... 607/7 |
| 5,514,160 | 5/1996 | Kroll et al. ..................... 607/5 |
| 5,601,612 | 2/1997 | Gliner et al. .................... 607/7 |
| 5,607,454 | 3/1997 | Cameron et al. ................. 607/5 |

FOREIGN PATENT DOCUMENTS

| | | | |
|---|---|---|---|
| WO 94/21327 | 9/1994 | WIPO | A61N 1/39 |
| WO 95/03087 | 2/1995 | WIPO | A61N 1/39 |

OTHER PUBLICATIONS

Geddes, L.A.; *Cardiovascular Devices and Their Applications*; John Wiley & Sons; pp. 300–319; 1984.

Geddes, L.A. and Tacker, W.A.; "Engineering and Physiological Considerations of Direct Capacitor–Discharge Ventricular Defibrillation"; Med. & Biol. Engng.; vol. 9; pp. 185–199; Pergamon Press; 1971.

Geddes, L.A.; Niebauer, M.J., Babbs, C.F.; and Bourland, J.D.; "Fundamental Criteria Underlying the Efficacy and Safety of Defibrillating Current Waveforms"; Med. & Biol. Eng. & Comp.; vol. 23; p. 122–130; 1985.

(List continued on next page.)

*Primary Examiner*—William E. Kamm
*Assistant Examiner*—George R. Evanisko
*Attorney, Agent, or Firm*—Fish & Richardson P.C.

[57] ABSTRACT

An electrotherapy circuit administers to a patient a current waveform. The electrotherapy circuit includes a charge storage device, at least two discharge electrodes connected by electrical circuitry to opposite poles of the charge storage device, a sensor that senses a patient-dependent electrical parameter (such as a patient impedance sensor), and a control circuit. The control circuit is connected to the sensor and the charge storage device and controls discharge of the charge storage device through the electrodes. The discharge of the charge storage device includes a current waveform having a sensing pulse portion, with insufficient energy for performing therapy, during which the sensor senses a patient-dependent electrical parameter (such as patient impedance), and a therapeutic discharge portion, with sufficient energy for performing therapy, having an initial discharge current controlled by the control circuit based on the patient-dependent electrical parameter (such as patient impedance) as sensed by the sensor. The sensing pulse portion has a discharge current that is at least about one-third of the initial discharge current of the therapeutic discharge portion.

53 Claims, 12 Drawing Sheets

OTHER PUBLICATIONS

Geddes, L.A.; Tacker, Jr., W.A.; Schoenlein, W.; Minton, M.; Grubbs, S.; and Wilcox, P.; "The Prediction of the Impedance of the Thorax to Defrillating Current"; Medical Instrumentation; V. 10, No. 3; May–Jun. 1976.

Jones, Douglas L. et al.; "Internal Cardiac Defibrillation in Man: Pronounced Improvement with Sequential Pulse Delivery to Two Different Lead Orientations"; Circulation; vol. 73, No. 3; pp. 484–491; Mar., 1986.

Jones, Janice L. et al.; "Decreased Arryhythmias in Cultured Myocardial Cells Following High Intensity Electric Field Stimulation with Biphasic Rectangular Waveforms"; Federation Proceedings Abs.; V. 42, N. 4; 1983.

Jones, Janice L. and Jones, Ronald E.; "Decreased Defibrillator–Induced Dysfunction with Biphasic Rectangular Waveforms"; The American Physiological Society; pp. H792–H796; 1984.

Jones, Janice L. and Jones, Ronald E.; "Defibrillator Waveshape Optimization"; Case Western Reserve University, Grant No: 5 R01 HL24606–03; Devices & Tech. Meeting, NIH; pp. 175; 1982.

Jones, Janice L. and Jones, Ronald E.; "Improved Defibrillator Waveform Safety Factor with Biphasic Waveforms"; The American Physiological Society; pp. H60–H65; 1983.

Jones, J.L.; Jones, R.E.; and Balasky, G.; "Reduced Excitation Threshold in Potassium Depolarized Myocardial Cells with Symmetrical Biphasic Waveforms"; J. of Mol. Cell. Cardiol.; vol. 17, Abst. No. 39; p. 27; 1985.

Kerber, Richard E. et al.; "Advance Prediction of Transthoracic Impedance in Human Defibrillation and Cardioversion"; Circulation; vol. 70, No. 2; pp. 303–308; Aug. 1984.

Kerber, Richard E. et al.; "Energy, Current, and Success in Defibrillation and Cardioversion: Clinical Studies Using an Automated Impedance–Based Method of Energy Adjustment"; Circulation; V. 77, No. 5; May, 1988.

Schuder, J.C.; Gold, J.H.; McDaniel, W.C.; Stoeckle, H.; Cheung, K.N.; "Asymmetrical Bidirectional Wave Defibrillation in Calves"; Proc. of the 35th Annual Conf. on Eng. in Medicine and Biology; V. 24; p. 41; 1982.

Schuder, John C.; McDaniel, Wayne C.; and Stoeckle, Harry; "Defibrillation of 100kg Calves with Asymmetrical Bidirectional, Rectangular Pulses"; Cardiovascular Research; vol. 18; pp. 419–426; 1984.

Schuder, John C.; Gold, Jerry H.; Stoeckle, Harry; "Development of Automatic Implanted Defibrillator"; University of Missouri; Grant No.: 5–ROL–HE–21674–04; Devices & Tech. Meeting, NIH; p. 206; 1981.

Schuder, John C. et al.; "Experimental Ventricular Defibrillation with an Automatic and Completely Implanted System"; Trans. Amer. Soc. Artif. Int. Organs; vol. 16; pp. 207–212; 1970.

Schuder, John C. et al.; "Transthoracic Ventricular Defibrillation in the 100 kg Calf with Symmetrical One–Cycle Bidirectional Rectangular Wave Stimuli"; IEEE Trans. on Biomedical Eng.; vol. BME–30, No. 7; Jul. 1983.

Schuder, John C. et al.; "Transthoracic Ventricular Defibrillation in the 100 kg Calf with Untruncated and Truncated Exponential Stimuli"; IEEE Transactions on Biomedical Engineering; V. BME–27, No. 1; Jan., 1980.

Schuder, J.C.; Gold, J.H.; and McDaniel, W.C.; "Ultrahigh--Energy Hydrogen Thyration/SCR Bidirectional Waveform Defibrillator"; Medical & Biological Engineering & Computing; vol. 20, pp. 419–424; Jul., 1982.

Tang, Anthony S.L. et al.; "Strength Duration Curve for Ventricular Defibrillation Using Biphasic Waveforms"; The North American Society of Pacing and Electrophysiology; PACE, vol. 10; p. 418; Mar.–Apr., 1987.

Tang, Anthony S.L. et al.; "Ventricular Defibrillation Using Biphasic Waveforms of Different Phasic Duration"; Pacing and Clinical Electrophysiology (PACE); vol. 10, No. 2; p. 417; Mar.–Apr., 1987.

Tang, Anthony S.L. et al.; "Ventricular Defibrillation Using Biphasic Waveforms: The Importance of Phasic Duration"; The American College of Cardiology; vol. 13, No. 1; pp. 207–214; Jan., 1989.

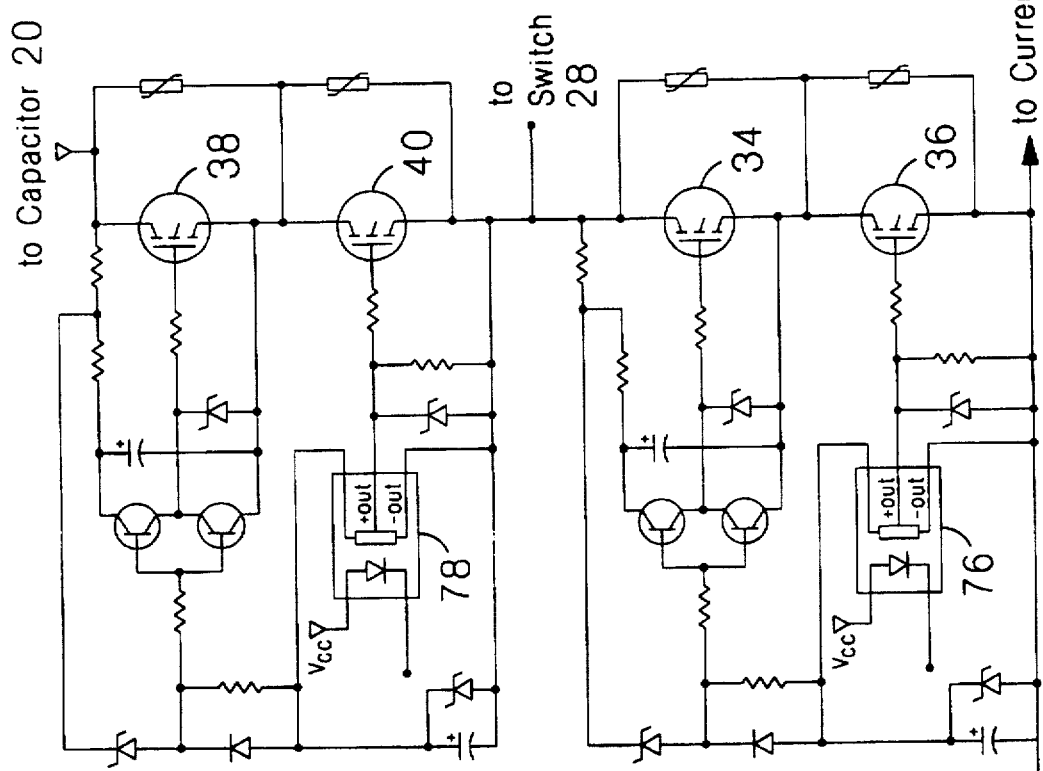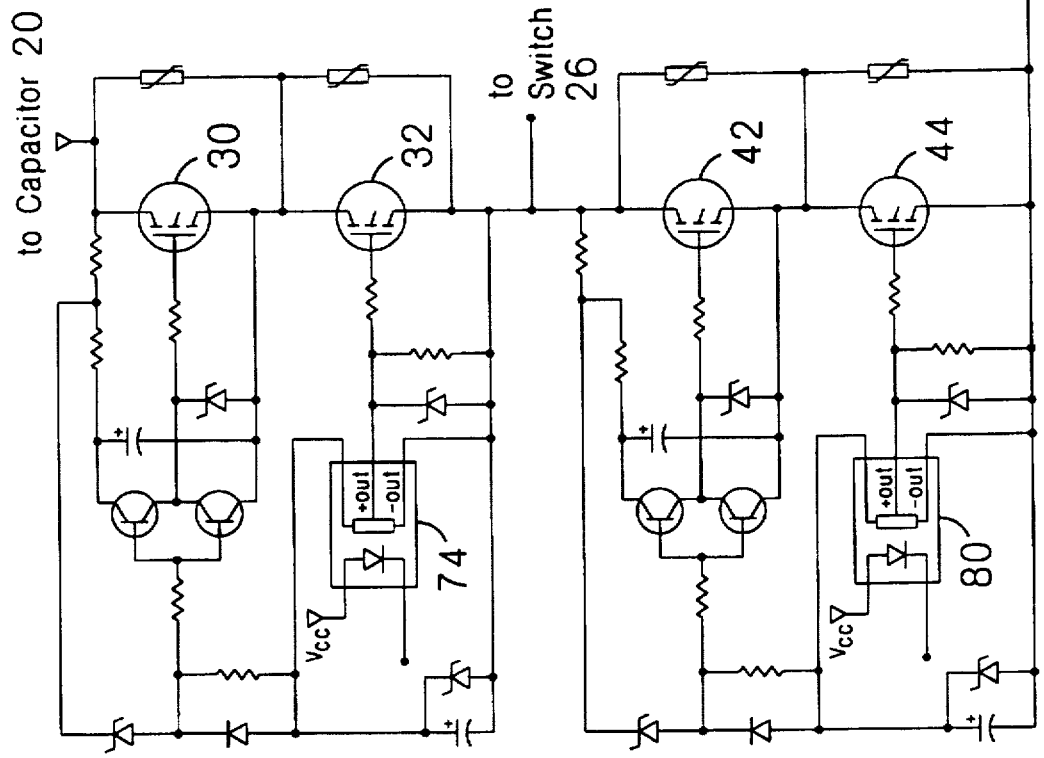
FIG. 4

Schedule 1: For 0 < $R_{pat}$ < 20 Ohms

| Time Interval Ms | 0.00-0.25 Imped. Test | 0.25-1.20 Initial Value | 1.20-2.40 Step 1 | 2.40-3.60 Step 2 | 3.60-4.80 Step 3 | 4.80-6.00 Step 4 | 6.1-10.1 Phase 2 |
|---|---|---|---|---|---|---|---|
| Normal Code | 7 | 7 | 6 | 5 | 4 | 3 | 3 |
| Resistance | 70 | 70 | 60 | 50 | 40 | 30 | 30 |
| KA Code | 7 | 7 | 6 | 5 | 4 | 3 | 3 |

Schedule 2: For 20 < $R_{pat}$ < 40 Ohms

| Time Interval Ms | 0.00-0.25 Imped. Test | 0.25-1.20 Initial Value | 1.20-2.40 Step 1 | 2.40-3.60 Step 2 | 3.60-4.80 Step 3 | 4.80-6.00 Step 4 | 6.1-10.1 Phase 2 |
|---|---|---|---|---|---|---|---|
| Normal Code | 7 | 6 | 5 | 4 | 3 | 2 | 2 |
| Resistance | 70 | 60 | 50 | 40 | 30 | 20 | 20 |
| KA Code | 7 | 6 | 5 | 4 | 3 | 2 | 1 |

Schedule 3: For 40 < $R_{pat}$ < 60 Ohms Normal Mode

| Time Interval Ms | 0.00-0.25 Imped. Test | 0.25-1.20 Initial Value | 1.20-2.40 Step 1 | 2.40-3.60 Step 2 | 3.60-4.80 Step 3 | 4.80-6.00 Step 4 | 6.1-10.1 N/A |
|---|---|---|---|---|---|---|---|
| Normal Code | 7 | 6 | 5 | 4 | 3 | 2 | N/A |
| Resistance | 70 | 60 | 50 | 40 | 30 | 20 | N/A |

Schedule 3A: For 40 < $R_{pat}$ < 60 Ohms Mode (Repeat of Schedule 5 Normal Mode)

| Time Interval Ms | 0.00-0.25 Imped. Test | 0.25-1.5 Initial Value | 1.5-3.0 Step 1 | 3.0-4.5 Step 2 | 4.5-6.0 Step 3 | 4.80-6.00 Step 4 | 6.1-10.1 Phase 2 |
|---|---|---|---|---|---|---|---|
| Code | 7 | 3 | 2 | 1 | 0 | N/A | 0 |
| Resistance | 70 | 30 | 20 | 10 | 0 | N/A | 0 |

FIG.10A

| Time Interval Ms | 0.00-0.25 Imped. Test | 0.25-1.20 Initial Value | 1.20-2.40 Step 1 | 2.40-3.60 Step 2 | 3.60-4.80 Step 3 | 4.80-6.00 Step 4 | 6.1-10.1 Phase 2 |
|---|---|---|---|---|---|---|---|
| Code | 7 | 1 | 1 | 2 | 1 | 0 | 0 |
| Resistance | 70 | 10 | 10 | 20 | 10 | 0 | 0 |

Schedule 4: For 60 < $R_{pat}$ < 85 Ohms
Normal Mode

| Time Interval Ms | 0.00-0.25 Imped. Test | 0.25-1.5 Initial Value | 1.5-3.0 Step 1 | 3.0-4.5 Step 2 | 4.5-6.0 Step 3 | | 6.1-10.1 Phase 2 |
|---|---|---|---|---|---|---|---|
| Code | 7 | 1 | 1 | 0 | 0 | N/A | 0 |
| Resistance | 70 | 10 | 10 | 0 | 0 | N/A | 0 |

Schedule 4A: For 60 < $R_{pat}$ < 85 Ohms
High-Energy Mode

| Time Interval Ms | 0.00-0.25 Imped. Test | 0.25-1.5 Initial Value | 1.5-3.0 Step 1 | 3.0-4.5 Step 2 | 4.5-6.0 Step 3 | | 6.1-10.1 Phase 2 |
|---|---|---|---|---|---|---|---|
| Code | 7 | 3 | 2 | 1 | 0 | N/A | 0 |
| Resistance | 70 | 30 | 20 | 10 | 0 | N/A | 0 |

Schedule 5: For 85 < $R_{pat}$ < 125 Ohms
Normal Mode

| Time Interval Ms | 0.00-0.25 Imped. Test | 0.25-1.5 Initial Value | 1.5-3.0 Step 1 | 3.0-4.5 Step 2 | 4.5-6.0 Step 3 | | 6.1-10.1 Phase 2 |
|---|---|---|---|---|---|---|---|
| Code | 7 | 0 | 0 | 0 | 0 | N/A | 0 |
| Resistance | 70 | 0 | 0 | 0 | 0 | N/A | 0 |

Schedule 5A: For 85 < $R_{pat}$ < 125 Ohms
High-Energy Mode

FIG. 10B

| | 15Ω | 25Ω | 50Ω | 75Ω | 100Ω | 125Ω |
|---|---|---|---|---|---|---|
| Phase 1 Current | 22.3 | 23 | 18.2 | 17.2 | 15 | 12.9 |
| Ripple | 4.0 | 4.3 | 2.5 | 2.0 | 1.5 | 1.2 |
| Tilt, % | 62 | 58 | 41 | 40 | 37 | 33 |
| Delivered Energy (Δ%), Normal Mode | N/A | 113(-25) | 142(-5) | 190(+27) | 193(+29) | 175(+17) |

Normal Mode

| | 15Ω | 25Ω | 50Ω | 75Ω | 100Ω | 125Ω |
|---|---|---|---|---|---|---|
| Phase 1 Current | 22.3 | 23 | 23 | 19.8 | 16.2 | 14 |
| Phase 1 Tilt, % of Avg | 11 | 4 | 22 | 50 | 59 | 43 |
| Ripple | 4.0 | 4.3 | 4 | 20 | 0 | 0 |
| Phase 2 Tilt, % | 62 | 58 | 50 | 41 | 44 | 25 |
| Delivered Energy (Δ%), Normal Mode | N/A | 113(-34) | 180(+6) | 222(+31) | 217(+28) | 199(=17) |

High-Energy Mode

FIG. 11

ELECTROTHERAPY CIRCUIT FOR PRODUCING THERAPEUTIC DISCHARGE WAVEFORM BASED ON HIGH-CURRENT SENSING PULSE

BACKGROUND OF THE INVENTION

This invention relates to electrotherapy circuits and more particularly relates to external defibrillators that apply defibrillation shocks to a patient's heart through electrodes placed externally on the patient's body or externally on the patient's heart during surgery.

Normally, electrochemical activity within a human heart causes the organ's muscle fibers to contract and relax in a synchronized manner. This synchronized action of the heart's musculature results in the effective pumping of blood from the ventricles to the body's vital organs. In the case of ventricular fibrillation (VF), however, abnormal electrical activity within the heart causes the individual muscle fibers to contract in an unsynchronized and chaotic way. As a result of this loss of synchronization, the heart loses its ability to effectively pump blood.

Defibrillators produce a large current pulse that disrupts the chaotic electrical activity of the heart associated with ventricular fibrillation and provide the heart's electrochemical system with the opportunity to resynchronize itself. Once organized electrical activity is restored, synchronized muscle contractions usually follow, leading to the restoration of effective cardiac pumping.

The current required for effective defibrillation is dependent upon the particular shape of the current waveform, including its amplitude, duration, shape (i.e., sine, damped sine, square, exponential decay), and whether the current waveform has a single polarity (monophasic) or has both positive and negative polarity (biphasic). It has been suggested that large defibrillation currents may cause damage to cardiac tissue, however.

It is known to construct an external defibrillator that can sense patient impedance and can set the durations of the first and second phases of a biphasic waveform as a function of the patient impedance. An example of such a defibrillator is described in PCT Patent Publication No. WO 95/05215. Fain et al., U.S. Pat. No. 5,230,336 discloses a method of setting pulse widths of monophasic and biphasic defibrillation waveforms based on measured patient impedance. Kerber et al., "Advance Prediction of Transthoracic Impedance in Human Defibrillation and Cardioversion: Importance of Impedance in Determining the Success of Low-Energy Shocks," 1984, discloses a method of selecting the energy of defibrillation shocks based on patient impedance measured using a high-frequency signal.

It is also known to construct a defibrillator with a safety resistor in the defibrillation path (PCT Patent Publication No. WO 95/05215). Before application of a defibrillation waveform to a patient, a test pulse is passed through the safety resistor while a current sensor monitors the current. If the sensed current is less than a safety threshold representative of a short circuit, the safety resistor is removed and the defibrillation waveform is applied to the patient.

It is known, in an implantable defibrillator, to use a biphasic waveform having a first phase consisting of multiple truncated decaying exponentials that form a sawtooth approximation of a rectilinear shape (Kroll, U.S. Pat. No. 5,199,429). This is accomplished by charging a set of energy storage capacitors and then successively allowing individual capacitors to discharge during the first phase, thereby creating the sawtooth pattern in the output current of the circuit.

A more recent patent, Kroll, U.S. Pat. No. 5,514,160, describes a biphasic waveform, in an implantable defibrillator, having a rectilinear-shaped first phase created by placing a MOSFET current limiter in the defibrillation path. This patent states that the grossly non-linear current limiter looks like a small and declining resistance to the capacitor. Also, Schuder et al., "Transthoracic Ventricular Defibrillation in the 100 kg Calf with Symmetrical One-Cycle Bidirectional Rectangular Wave Stimuli" describes the use of biphasic waveforms having rectilinear first and second phases to reverse ventricular fibrillation in calves. Stroetmann et al., U.S. Pat. No. 5,350,403, discloses a waveform having a sawtooth ripple that is formed by periodically interrupting a non-continuous discharge of a charging circuit.

SUMMARY OF THE INVENTION

The invention features an electrotherapy circuit for administering to a patient a current waveform such as a defibrillation waveform. The electrotherapy circuit includes a charge storage device, at least two discharge electrodes connected by electrical circuitry to opposite poles of the charge storage device, a sensor that senses a patient-dependent electrical parameter (such as a patient impedance sensor), and a control circuit. The control circuit is connected to the sensor and the charge storage device and controls discharge of the charge storage device through the electrodes. The discharge of the charge storage device includes a current waveform having a sensing pulse portion, with insufficient energy for performing therapy, during which the sensor senses a patient-dependent electrical parameter (such as patient impedance), and a therapeutic discharge portion, with sufficient energy for performing therapy, having an initial discharge current controlled by the control circuit based on the patient-dependent electrical parameter (such as patient impedance) as sensed by the sensor. The sensing pulse portion has a discharge current that is at least about one-third of the initial discharge current of the therapeutic discharge portion.

The impedance of a patient when a large direct current is passing through the patient is different from the impedance of the patient when a small current is passing through the patient or when an alternating current is passing through the patient. We believe that the current level of the sensing portion should always be at least one-third, and more preferably one-half, of the current level at the beginning of the therapeutic discharge portion in order to ensure detection of a patient impedance that is similar to the impedance of the patient during the therapeutic discharge portion.

By controlling the discharge of the charge storage device based on the sensed patient impedance, it is possible to limit the difference in the peak current that passes through a low-impedance patient as compared with a high-impedance patient. Thus, the current is made more constant over a range of patient impedances, and the electrotherapy circuit provides effective defibrillation while maintaining controlled current levels to reduce any possibility of damage to heart, skin, and muscle tissue.

In preferred embodiments the control circuit controls the discharge of the charge storage device by controlling the resistance of a resistive circuit connected between the charge storage device and one of the electrodes. The resistive circuit includes a set of resistors connected together in series.

In preferred embodiments the control circuit decides, based on the patient impedance sensed during an initial sensing pulse portion of the discharge of the charge storage device, how many (if any) resistors to include in the defibrillation path at the beginning of a therapeutic discharge portion of the discharge of the charge storage device (e.g., at the beginning of a biphasic defibrillation waveform). This may mean, depending on the sensed patient impedance, that the current level steps up from the sensing pulse to the beginning of the biphasic defibrillation waveform. Once the biphasic defibrillation waveform begins, the resistors that are present in the defibrillation path are successively shorted out, thereby creating a sawtooth approximation to a rectilinear shape in the output current (output decays and then jumps up every time a resistor is shorted out) and compensating for the decreasing capacitor voltage.

This provides an improved, low-cost way of creating a biphasic waveform having a rectilinear first phase. Resistors are relatively inexpensive as compared with capacitors, and a total of N steps in resistance values can be obtained with $\log_2 N$ resistors, as opposed to N capacitors, simply by connecting the resistors in series in a binary sequence (1-2-4-etc.). Because resistors are used instead of capacitors, no circuitry is required to equalize voltages on capacitors upon recharge or to prevent reversal of voltages on capacitors.

Certain embodiments include a variable resistor stage that tends to smooth out the sawtooth pattern. The variable resistor stage is a circuit that is reset to its maximum resistance value every time one of the fixed-value resistors is shorted out and then decreases to zero over the time interval before the next resistance step reduction.

Another advantage of the invention is that the resistors in the defibrillation path inherently protect against possible short circuits.

We believe that the use of a waveform having a substantially rectilinear positive phase tends to provide a lower threshold of average current required for effective defibrillation, and tends to avoid damaging the patient's tissue even if the total energy applied to the patient is relatively high. We also believe that any sawtooth ripple in either phase of the waveform should preferably have a height less than about one-quarter of the average height of the phase, and more preferably less than about one-sixth of the average height of the phase, in order to further minimize the threshold of average current required for effective defibrillation and the possibility of damaging the patient's tissue.

Preferably, the discharge of the charge storage device occurs without recharging of the charge storage device between the sensing pulse portion and the therapeutic discharge portion of the current waveform. Thus, it is possible to apply paddles to the chest of the patient (or apply hand-held spoons directly to the patient's heart during open heart surgery) and immediately discharge the sensing pulse and then discharge the biphasic defibrillation waveform immediately after the sensing pulse. This is particularly important because the patient (or the patient's heart) may move and because it is difficult for a practitioner to apply a constant force to the patient's skin (or the patient's heart).

Numerous other features, objects, and advantages of the invention will become apparent from the following detailed description when read in connection with the accompanying drawings.

BRIEF DESCRIPTION OF THE DRAWINGS

FIG. 4 is a schematic diagram of the H-bridge circuit shown in the electrotherapy circuit of FIG. 2.

FIG. 10 is a set of schedules of the resistance values used for generating the waveforms shown in FIGS. 6–10.

FIG. 11 is a table of waveform parameters for various patient impedances in a "normal" mode of operation and a "high-energy" mode of operation of an electrotherapy circuit according to the invention.

DETAILED DESCRIPTION

Figure 1:
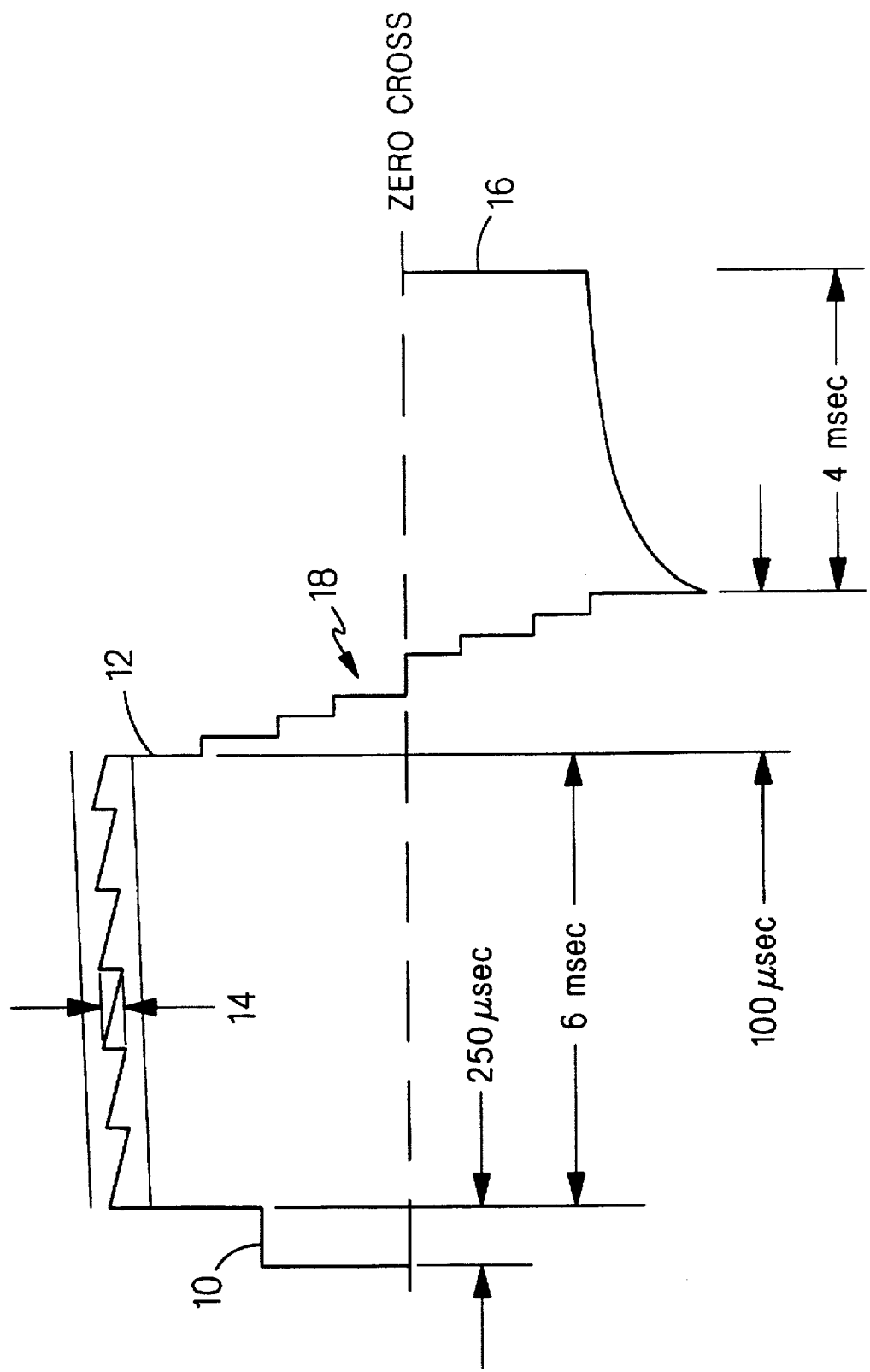
FIG. 1 is a diagram of a current waveform produced by a electrotherapy circuit according to the invention.

With reference to FIG. 1, in operation of an external defibrillator according to the invention, the biphasic current waveform begins with an initial "sensing pulse" 10, which has insufficient energy for performing therapy. The sensing pulse is integral with, i.e., immediately followed by, a biphasic defibrillation waveform having sufficient energy for defibrillating the patient's heart. The biphasic defibrillation waveform includes a six-millisecond, generally rectilinear positive phase 12 having a sawtooth ripple 14, which is in turn followed by a four millisecond negative phase 16 that decays exponentially until the waveform is truncated. As used herein, the term "rectilinear" means having a straight line, regardless of whether the straight line is flat or slightly tilted. The current waveform decreases through a series of steps 18 from the end of the positive phase to the beginning of negative phase, one of the steps being at the zero crossing. Note that for purposes of clarity this 0.1-millisecond transition is not drawn to scale in FIG. 1; if drawn to scale the duration of this transition would be much shorter than shown in FIG. 1.

We believe that a biphasic defibrillation waveform having a positive rectilinear pulse of 6 milliseconds duration followed by 0.1-millisecond transition and a 4 millisecond negative pulse having an initial amplitude equal to the final amplitude of the positive pulse is an especially effective waveform for defibrillation. The negative pulse does not need to be rectilinear.

Figure 2:
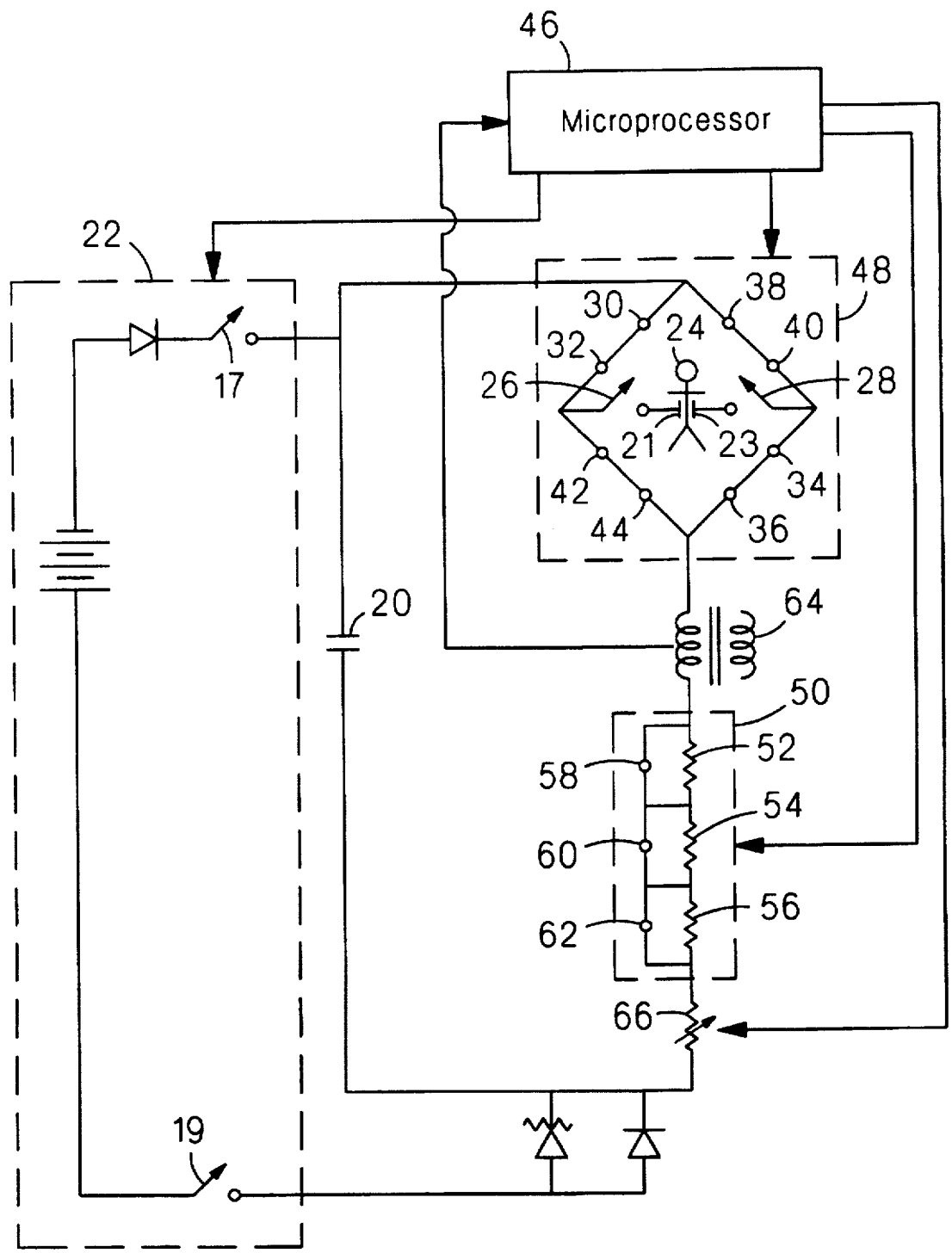
FIG. 2 is a diagram of the key elements of electrotherapy circuit according to the invention.

The basic circuitry for producing the biphasic waveform is shown in FIG. 2. A storage capacitor 20 (115 µF) is charged to a maximum of 2200 volts by a charging circuit 22 while relays 26 and 28 and the H-bridge are open, and then the electric charge stored in storage capacitor 20 is allowed to pass through electrodes 21 and 23 and the body of a patient 24. In particular, relay switches 17 and 19 are opened, and then relay switches 26 and 28 are closed. Then, electronic switches 30, 32, 34, and 36 of H-bridge 48 are closed to allow the electric current to pass through the patient's body in one direction, after which electronic H-bridge switches 30, 32, 34, and 36 are opened and H-bridge switches 38, 40, 42, and 44 are closed to allow the electric current to pass through the patient's body in the opposite direction. Electronic switches 30–44 are controlled by signals from respective opto-isolators, which are in turn controlled by signals from a microprocessor 46, or alternatively a hard-wired processor circuit. Relay switches 26, and 28, which are also controlled by microprocessor 46, isolate patient 24 from leakage currents of bridge switches 30–44, which may be about 500 micro-amps. Relay switches 26 and 28 may be relatively inexpensive because they do not have to "hot switch" the current pulse. They close a few milliseconds before H-bridge 48 is "fired" by closure of some of the H-bridge switches.

Electrodes 21 and 23 may be standard defibrillation electrodes having flat surfaces that adhere to the chest of the patient, but they may alternatively be hand-held paddles that are applied to the chest of the patient or hand-held spoons that are applied directly to the patient's heart during open heart surgery. Storage capacitor 20 may be a single capacitor or a set of series-connected or parallel-connected capacitors.

A resistive circuit 50 that includes series-connected resistors 52, 54, and 56 is provided in the current path, each of the resistors being connected in parallel with a shorting switch 58, 60, and 62 controlled by microprocessor 46. The resistors are of unequal value, stepped in a binary sequence to yield $2^n$ possible resistances where n is the number of resistors. During the initial "sensing pulse," when H-bridge switches 30, 32, 34, and 36 are closed, all of the resistor-shorting switches 58, 60, and 62 are in an open state so that the current passes through all of the resistors in series. Current-sensing transformer 64 senses the current passing through the patient 24, from which microprocessor 46 determines the resistance of the patient 24.

The initial sensing pulse is integral with, i.e., immediately followed by, a biphasic defibrillation waveform, and no re-charging of storage capacitor 20 occurs between the initial sensing pulse and the biphasic defibrillation waveform.

If the patient resistance sensed during the initial sensing pulse is low, all of the resistor-shorting switches 58, 60, and 62 are left open at the end of the sensing pulse so that all of the resistors 52, 54, and 56 remain in the current path (the resistors are then successively shorted out during the positive phase of the biphasic defibrillation waveform in the manner described below in order to approximate a rectilinear positive phase). Thus, the current at the beginning of the positive first phase 12 of the biphasic defibrillation waveform is the same as the current during sensing pulse 10. If the patient resistance sensed during the sensing pulse is high, some or all of the resistor-shorting switches 58, 60, and 62 are closed at the end of the sensing pulse, thereby shorting out some or all of the resistors. This causes an upward jump in current at the end of the sensing pulse as shown in the waveform in FIG. 1.

Thus, immediately after the sensing pulse, the biphasic defibrillation waveform has an initial discharge current that is controlled by microprocessor 46 based on the patient impedance sensed by current-sensing transformer 64.

The current level of the sensing pulse is always at least 50 percent of the current level at the beginning of positive first phase 12, and the sensing pulse, like the defibrillation pulse, is of course a direct-current pulse.

By appropriately selecting the number of resistors that remain in the current path, microprocessor 46 reduces (but does not eliminate) the dependence of peak discharge current on patient impedance, for a given amount of charge stored by the charge storage device. For a patient resistance of 15 ohms the peak current is about 25 amps, whereas for a patient resistance of 125 ohms the peak current is about 12.5 amps (a typical patient impedance is about 75 ohms).

During the positive phase of the biphasic waveform some or all of the resistors 52, 54, and 56 that remain in series with the patient 24 are successively shorted out. Every time one of the resistors is shorted out, an upward jump in current occurs in the waveform, thereby resulting in the sawtooth ripple shown in the waveform of FIG. 1. The ripple tends to be greatest at the end of the rectilinear phase because the time constant of decay (RC) is shorter at the end of the phase than at the beginning of the phase. Of course, if all of the resistors have already been shorted out immediately after the end of the sensing pulse, the positive phase of the biphasic waveform simply decays exponentially until the waveform switches to the negative phase.

As is shown in FIG. 1, at the end of the positive phase, the current waveform decreases through a series of rapid steps from the end of the positive phase to the beginning of negative phase, one of the steps being at the zero crossing. Microprocessor 46 accomplishes this by 1) successively increasing the resistance of resistive circuit 50 in fixed increments through manipulation of resistor-shorting switches 58, 60, and 62, then 2) opening all of the switches in H-bridge 48 to bring the current waveform down to the zero crossing, then 3) reversing the polarity of the current waveform by closing the H-bridge switches that had previously been open in the positive phase of the current waveform, and then 4) successively decreasing the resistance of resistance circuit 50 in fixed increments through manipulation of resistor-shorting switches 58, 60, and 62 until the resistance of resistance circuit 50 is the same as it was at the end of the positive phase.

In one embodiment a variable resistor 66 is provided in series with the other resistors 52, 54, and 56 to reduce the sawtooth ripple. Every time one of the fixed-value resistors 52, 54, or 56 is shorted out, the resistance of variable resistor 66 automatically jumps to a high value and then decreases until the next fixed-value resistor is shorted out. This tends, to some extent, to smooth out the height of the sawtooth ripple from about 3 amps to about 0.1 to 0.2 amps, and reduces the need for smaller increments of the fixed-value resistors (i.e., it reduces the need for additional fixed-value resistor stages).

The rectilinear phase may exhibit a degree of tilt, either slightly up, or slightly down. This occurs because of the "graininess" of the steps, because patient impedance may change during the waveform, and because of inherent inaccuracies of circuit elements. For example, with respect to graininess of the steps, calculations might show that, for a 50-ohm patient, the optimal resistance required at the end of the rectilinear phase is 14 ohms, in which case we must choose between 10 or 20 ohms based on the available fixed-value resistors. If we choose 10 ohms, an "error" of 4 ohms would result at the end of the rectilinear phase, and the current would rise by about 6 or 7 percent [(14−10)/(50+14)] by the end of the phase. Thus, a 15 amp rectilinear pulse would rise from 15 amps to 16 amps over the rectilinear phase. If it were considered desirable to change this rise to a droop, the microprocessor could easily accommodate such a change. In general, we believe it is desirable to avoid tilt greater than about 20 percent in order to avoid passage of excessive current through the patient's body at the high end of the tilt.

The choices of capacitor (115 µF) and voltage (2200 volts) are based on the desired current requirements and allowable droop during the negative phase. The capacitor stores the minimum energy required to meet the delivered charge requirements (i.e., the charge required to produce the desired current waveform having the desired duration).

The switches in the left-hand side of H-bridge 48 can be tested by closing switches 17 and 19, opening switches 26 and 28, closing switches 30 and 32, then after a short time closing switches 42 and 44, then after a short time opening switches 30 and 32, and then after a short time opening switches 42 and 44. If the switches are working properly, current-sensing transformer 64 will sense the passage of current when all four switches are closed, and will sense no current when switches 30 and 32 or switches 42 and 44 are open. Otherwise, current-sensing transformer 64 will detect the possible presence of a short circuit or an open circuit. Similarly, the switches in the right-hand side of H-bridge 48 can be tested by closing switches 38 and 40, then after a short time closing switches 34 and 36, then after a short time opening switches 38 and 40, and then after a short time opening switches 34 and 36. This valuable safety test does not require current to pass through the patient, due to the placement of current-sensing transformer 64 outside the legs of H-bridge 48.

Microprocessor 46 easily accommodates a complex environment and functions in harmony with various controls, interlocks, and safety features of the electrotherapy system. In addition to performing the functions described herein, the microprocessor may operate a strip chart, a pacer, an ecg monitor, etc. In the event that additional research should show that the characteristics of current pulses should be different from those described herein, the microprocessor can be re-programmed to alter the current waveforms applied to the patient. For example, the microprocessor could accommodate a waveform change to produce a rising or falling rectilinear ramp voltage with time, or a waveform having a negative phase amplitude less than (or greater than) the positive phase amplitude. Of course, the storage capacitor must have enough stored charge to support the required output.

In an alternative embodiment the negative phase of the current waveform is substantially rectilinear, rather than exponentially decaying, and the techniques described above for providing a substantially rectilinear positive phase would be extended to produce the substantially rectilinear negative phase. Such a substantially rectilinear negative phase would require the use of a higher capacitance and voltage and higher-rated switching devices than those employed in the circuit of FIG. 2 (for a given initial current value of the negative phase).

Figure 3:
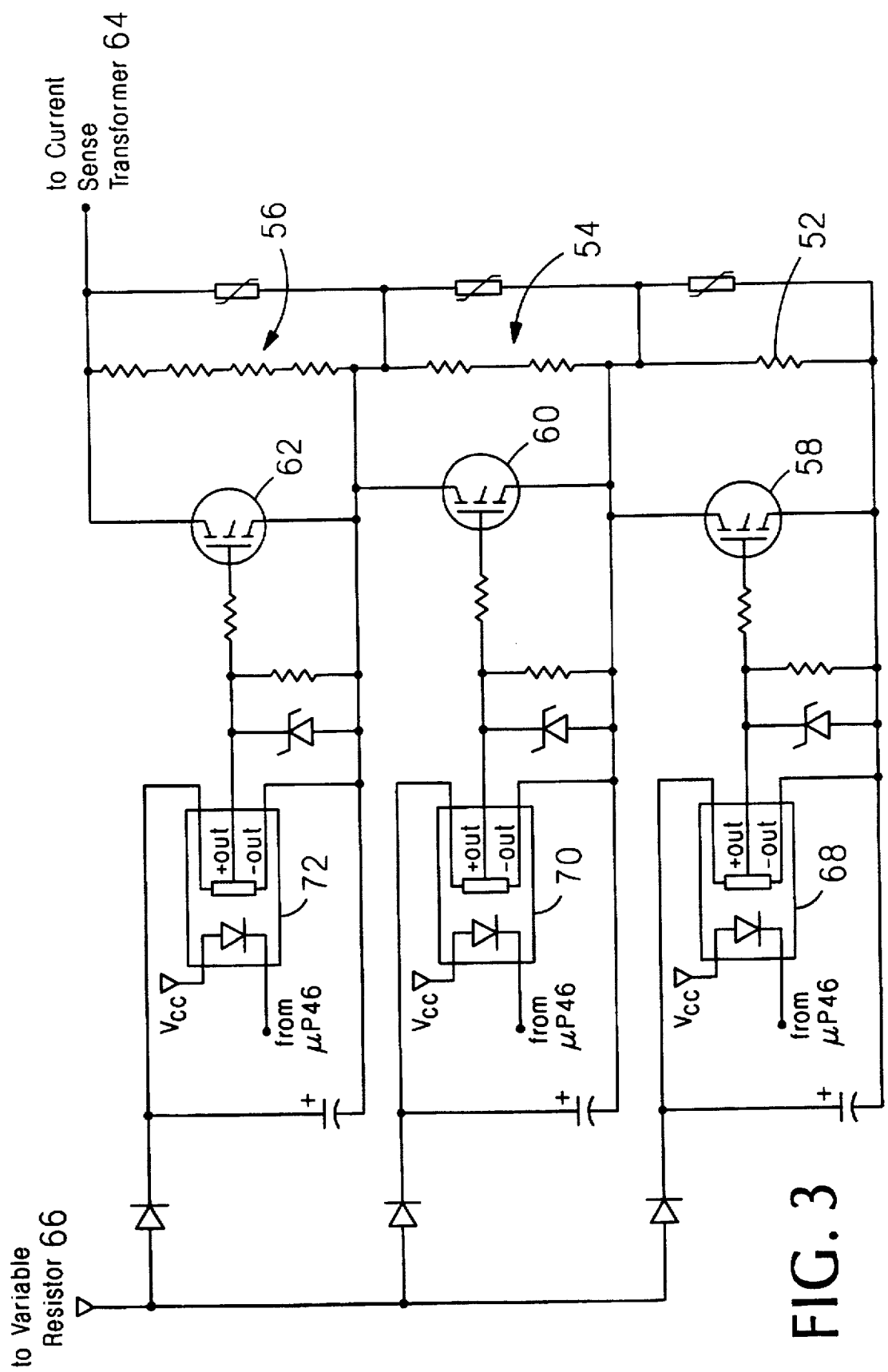
FIG. 3 is a schematic diagram of the series-connected resistor circuit shown in the electrotherapy circuit of FIG. 2.

Referring to FIG. 3, the resistive circuit 50 of FIG. 2 includes resistors 52 (10 ohms), 54 (two 10-ohm resistors), and 56 (four 10-ohm resistors) and IGBT shorting switches 58, 60, and 62. Alternatively, other semiconductor switching devices may be used. The resistor string is designed to switch in 10-ohm steps. This allows for a maximum resistance of 80-ohms (including the 10-ohm variable resistor), which makes it possible to limit patient current to 21.5 amps for a 15-ohm patient resistance (the current pulse would be 25.6 amps in the event of a short circuit between the electrodes).

The values of the resistors, as well as the 115 µF value of the storage capacitor and the capacitor voltage of 2200 volts, are determined by the current required to be delivered into the patient load (about 12.5–25 amps) and the range of the patient load (e.g., 125 ohms–15 ohms). The IGBT shorting switches are switched on and off by means of opto-isolator circuits 68, 70, and 72 controlled by the microprocessor. Referring to FIG. 4, H-bridge 48 of FIG. 2 includes IGBT switches 30–44 similarly switched on and off by means of opto-isolator circuits 74, 76, 78, and 80 controlled by the microprocessor. Alternatively, switches 30–44 may be other types of semiconductor switching devices. Only one opto-isolator is provided to control each pair of switches in each arm of the H-bridge.

Figure 5:
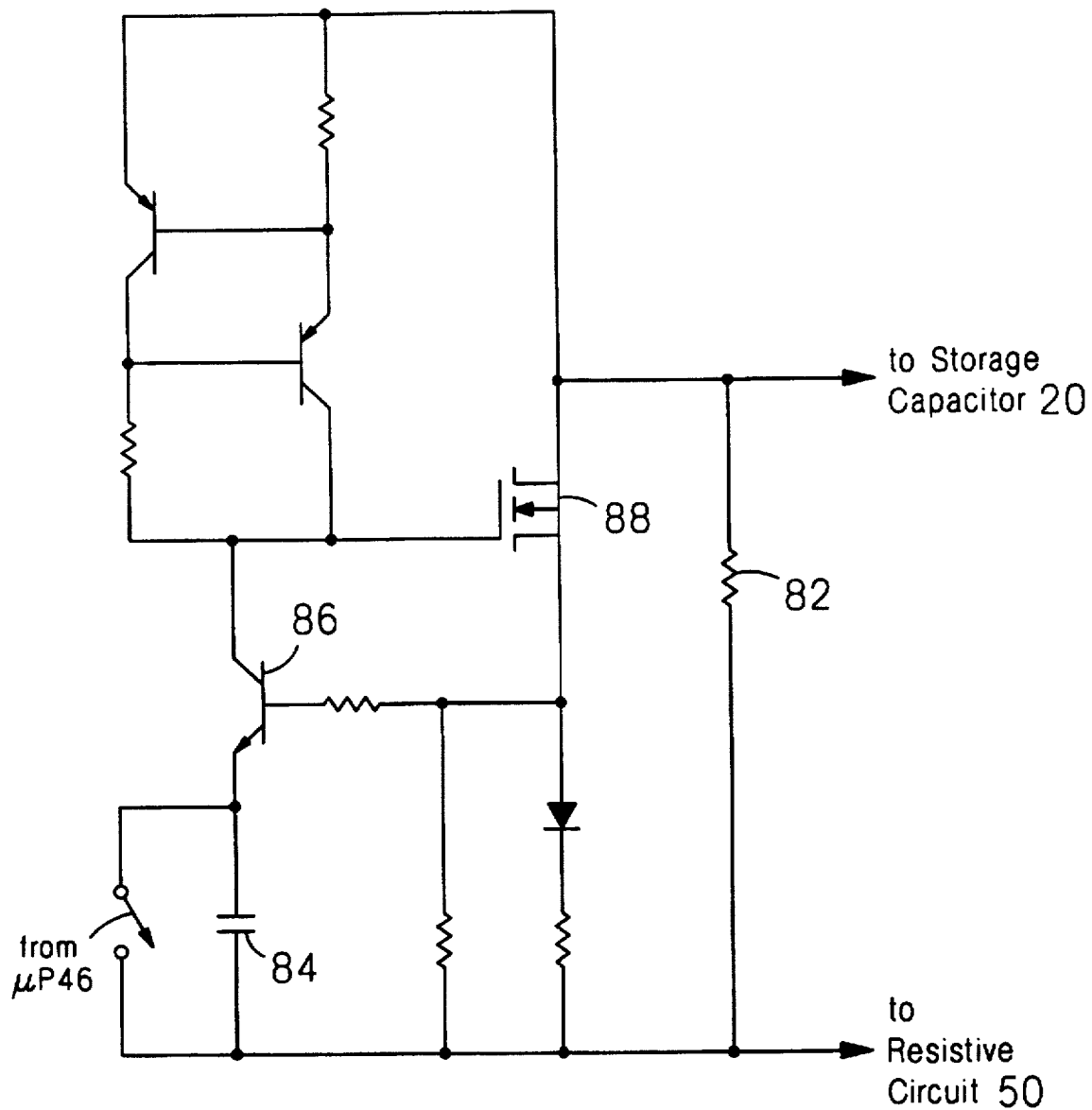
FIG. 5 is a schematic diagram of the variable resistor shown in the electrotherapy circuit of FIG. 2.

Referring to FIG. 5, variable resistor 66 of FIG. 2 includes resistor 82 connected between resistive circuit 50 and storage capacitor 20. The effective resistance of variable resistor 66 is controlled by the circuitry connected in parallel with resistor 82, through which some of the current from storage capacitor 20 to resistive circuit 50 can pass.

In particular, whenever the microprocessor shorts out one of the fixed-value resistors in resistive circuit 50, it also shorts capacitor 84. This causes transistor 86 to turn on, which pulls the gate of FET or IGBT transistor 88 to ground, thereby turning transistor 88 off. Because transistor 88 is turned off, all of the current from storage capacitor 20 to resistive circuit 50 passes through resistor 82.

Capacitor 84 then begins to charge linearly because of the current source in the collector of transistor 86. This causes the voltage at the drain/collector of transistor 88 to increase linearly, which causes the current in transistor 88 to increase linearly. When the current in transistor 88 increases, the current passing through resistor 82 decreases, thereby reducing the voltage across resistor 82 and therefore reducing the effective resistance of variable resistor 66.

The electrotherapy circuit can be operated in either a "normal" mode of operation or a "high-energy" mode of operation. These two modes of operation are identical when the sensed patient impedance is below 40 ohms. If the sensed patient impedance is above 40 ohms, however, the microprocessor selects an initial resistance value of the series-connected resistors (after the sensing pulse) that depends on the mode of operation. In particular, in the "high-energy" mode of operation the microprocessor selects a lower initial resistance than in the "normal" mode of operation. Thus, more energy will be delivered to the patient in the "high-energy" mode of operation than in the "normal" mode of operation. A practitioner may try to defibrillate in the "normal" mode, then switch to the "high-energy" mode if unsuccessful.

In the "high-energy" mode of operation of the circuit, if the sensed patient impedance is sufficiently high (above 85 ohms) all of the resistor-shorting switches are closed after the initial "sensing pulse," thereby shorting out all of the series-connected resistors. This causes an upward jump at the end of the "sensing pulse," after which the positive and negative phases of the biphasic waveform both decay exponentially.

Figure 6:
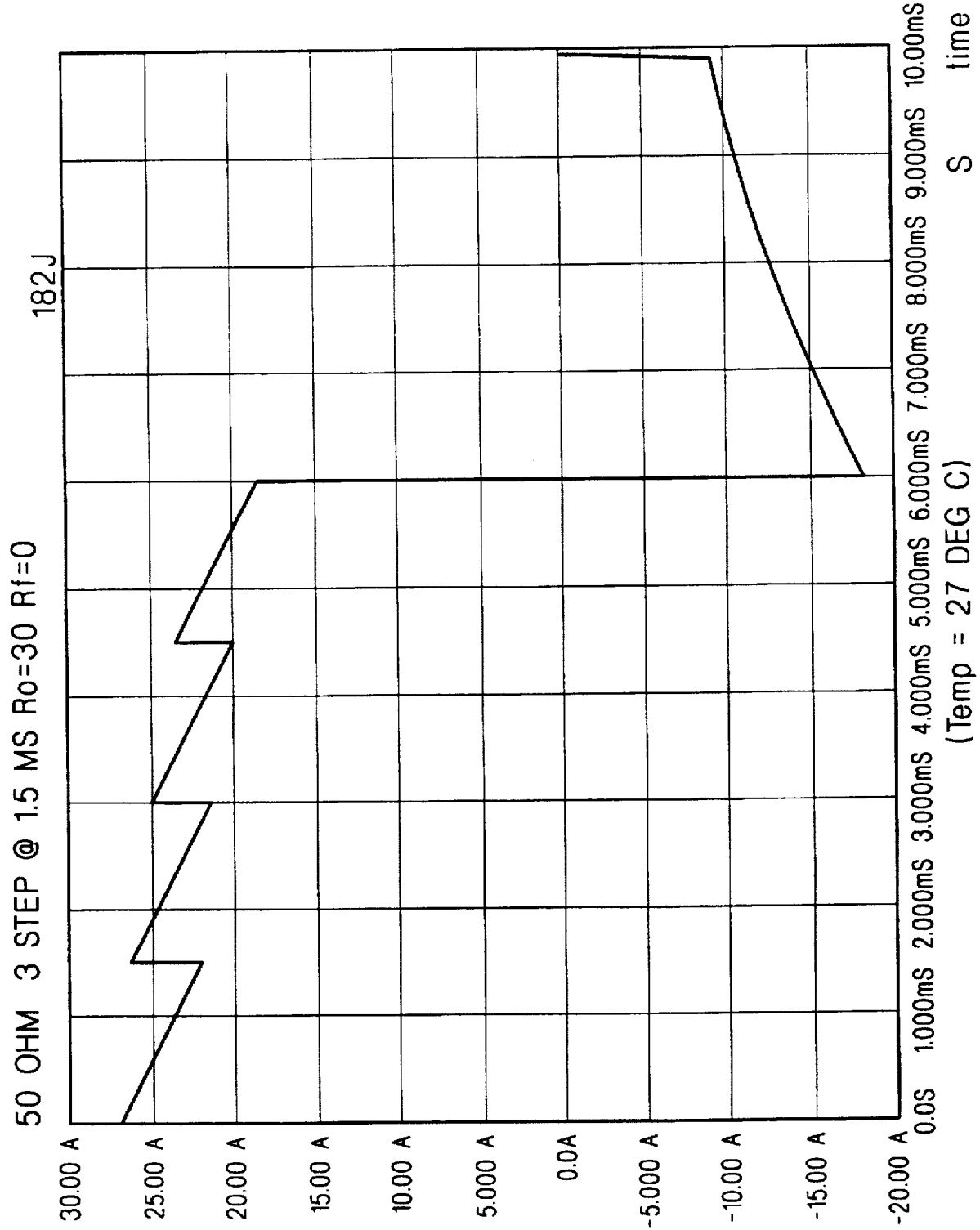
FIGS. 6–9 are diagrams of current waveforms produced by an electrotherapy circuit according to the invention based on different measured patient impedances.
Figure 7:
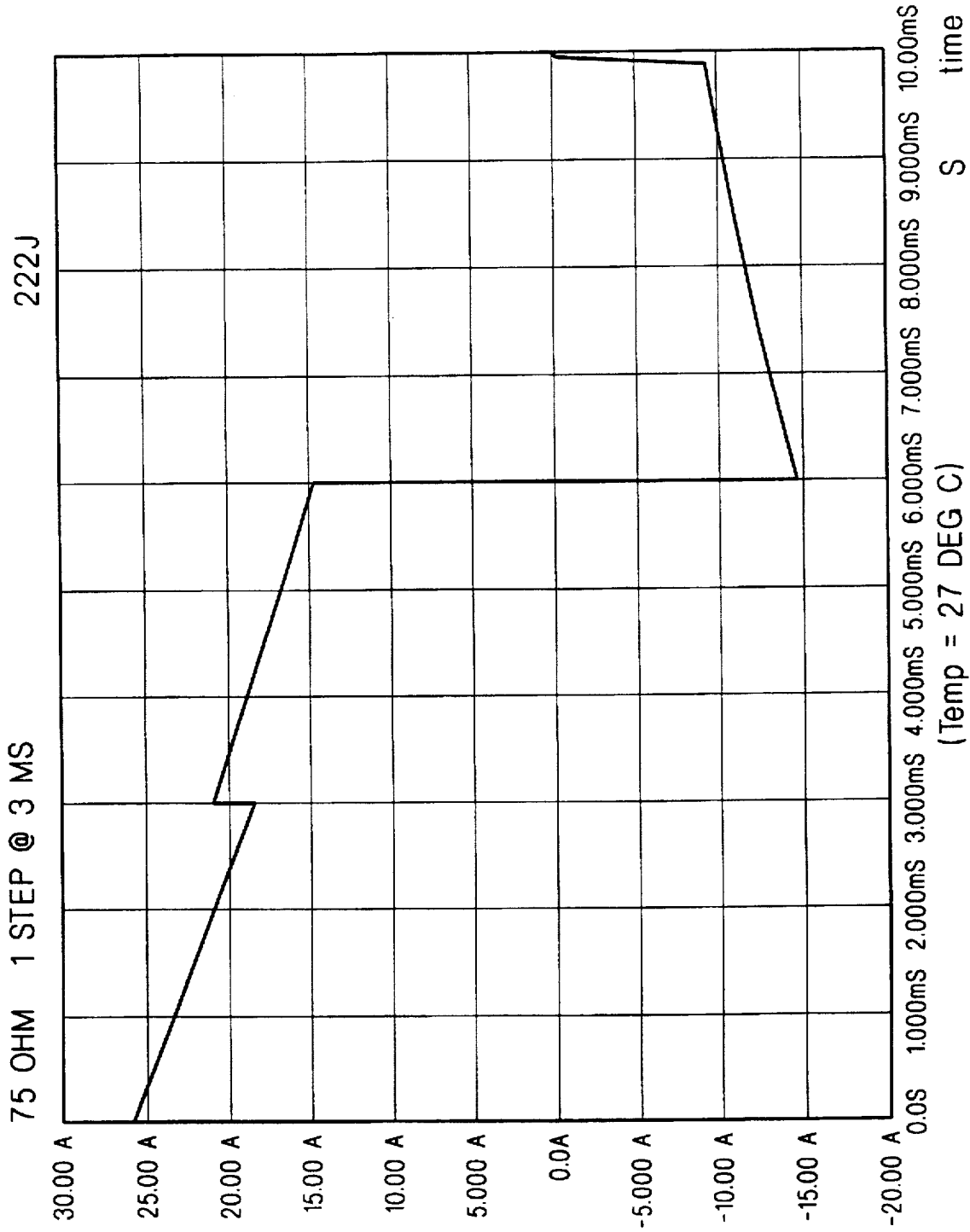
Figure 8:
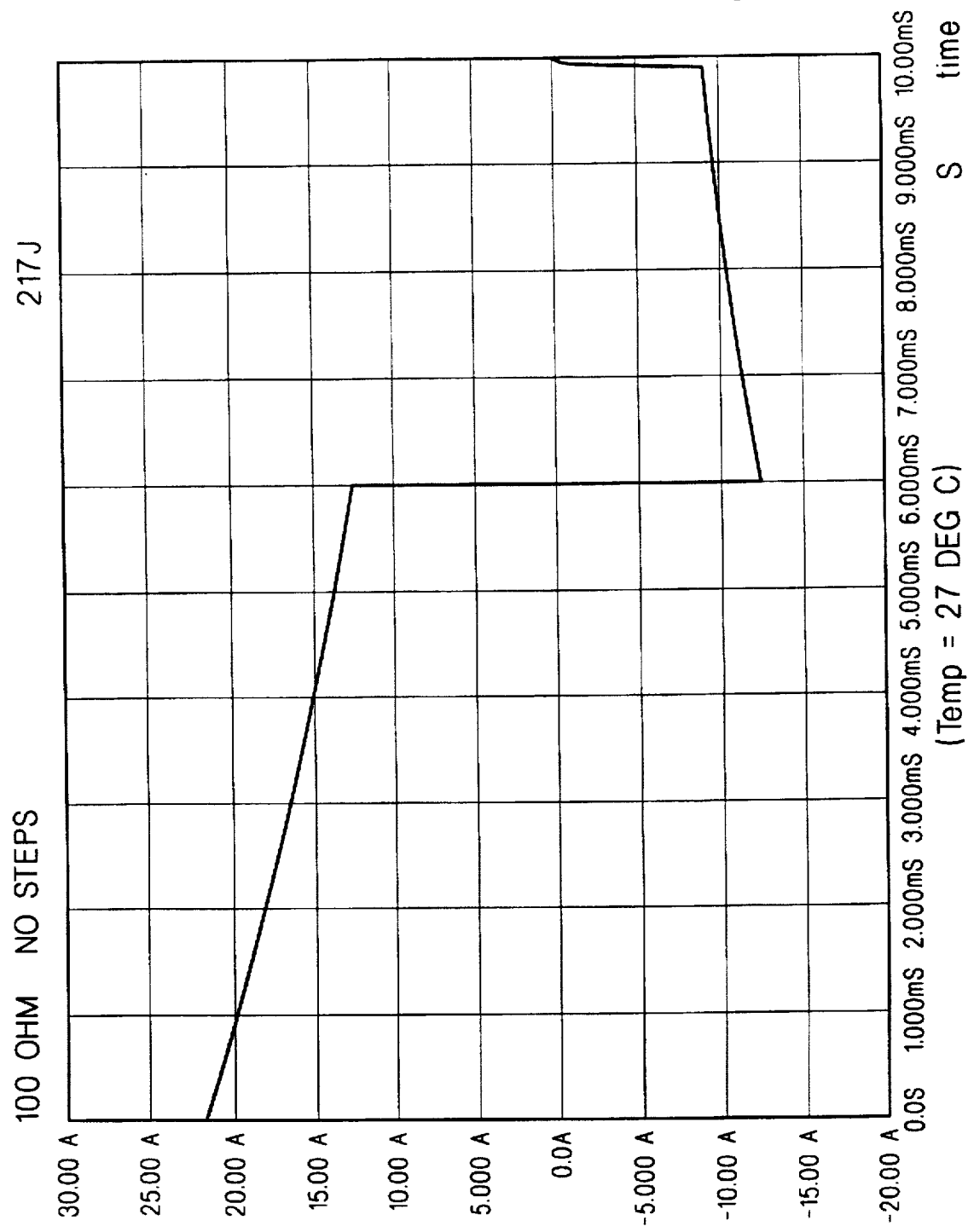
Figure 9:
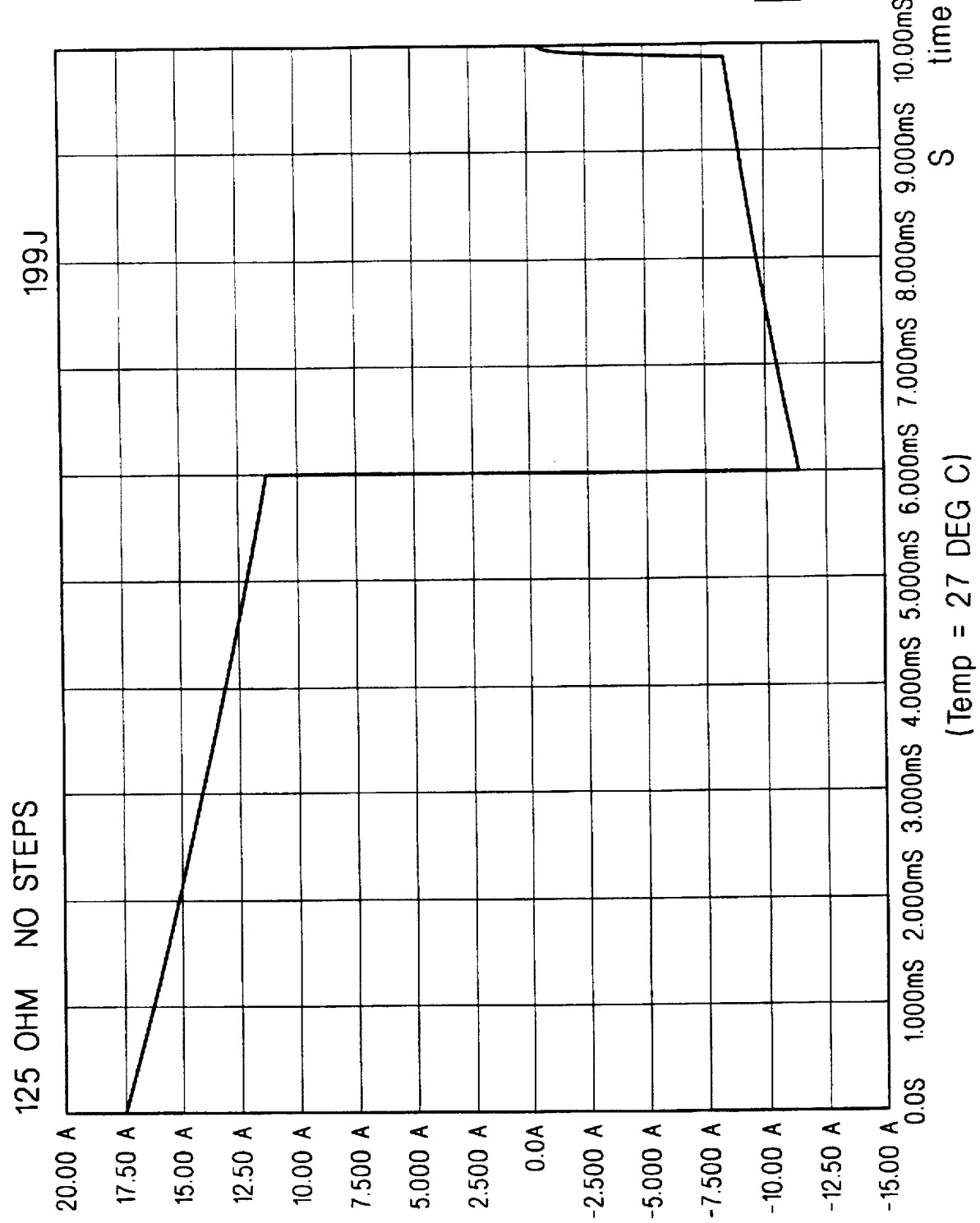

Referring to the table of FIG. 10 and the waveforms of FIGS. 6–9, which correspond to certain schedules in the table of FIG. 10, the microprocessor schedules the resistance values of the series-connected resistors based on the measured patient impedance, in a manner such that the stepwise resistance decrease of the series-connected resistors over the course of the rectilinear phase matches the decrease in voltage of the storage capacitor. For the sake of simplicity, the initial sensing pulse and the series of steps between the end of the positive phase and the beginning of negative phase have been omitted from FIGS. 6–9, and it is assumed the variable resistor discussed above is not used. FIGS. 6–9 are all examples of the "high-energy" mode. FIG. 6, which corresponds to Schedule 3A in FIG. 10, is based on a patient impedance of 50 ohms, in which case the microprocessor selects an initial series-connected resistance of 30 ohms and a residual series-connected resistance of 0 ohms at the end of the positive phase. The total energy delivered to the patient is about 182 joules. FIG. 7, corresponding to Schedule 4A, is based on a patient impedance of 75 ohms, an initial resistance of 10 ohms, a residual resistance of 0 ohms, and an energy of 222 joules. FIG. 8, corresponding to Schedule 5A, is based on a patient impedance of 100 ohms, an initial resistance of 0 ohms, and a residual resistance of 0 ohms, and an energy of 217 joules. FIG. 9, corresponding to Schedule 5A, is based on a patient impedance of 125 ohms, an initial resistance of 40 ohms, a residual resistance of 0 ohms, and an energy of 199 joules.

FIG. 11 includes a table, corresponding to the "normal" mode of operation, that identifies, as a function of the patient impedance, the positive-phase current (in amps), ripple (in amps, assuming the variable resistor is not used), tilt of the negative phase (expressed as a percentage of the initial current value of the negative phase), total delivered energy (in joules), and the deviation of the total delivered energy from the normal mode's "rating" of 150 joules. FIG. 11 also includes a similar table for the "high-energy" mode of operation, identifying positive-phase current, tilt of the positive phase (based on a straight-line average through the ripples), ripple, tilt of the negative phase, total delivered energy, and the deviation of the total delivered energy from the "rating" of 170 joules.

In both the high-energy and normal modes described above, the storage capacitor is charged to its maximum voltage of 2200 volts. Other modes of operation can be developed in which the storage capacitor is charged to a lesser voltage, or in which different resistance schedules are used.

There have been described novel and improved electrotherapy circuits and techniques for using them. It is evident that those skilled in the art may now make numerous uses and modifications of and departures from the specific embodiment described herein without departing from the inventive concept. For example, the techniques described herein can be used in connection with implantable defibrillators rather than external defibrillators or in connection with electrotherapy circuits other than defibrillator circuits or even circuits that perform functions other than electrotherapy.

What is claimed is:

1. An electrotherapy circuit for administering to a patient a current waveform, comprising:
   a charge storage device having opposite poles;
   at least two discharge electrodes connected by electrical circuitry to the opposite poles of the charge storage device;
   a sensor that senses a patient-dependent electrical parameter during a sensing pulse portion of a current waveform, the sensing pulse portion having insufficient energy for performing therapy; and
   a control circuit, connected to the sensor and the charge storage device, for controlling discharge of the charge storage device through the electrodes, the discharge of the charge storage device comprising the current waveform having the sensing pulse portion during which the sensor senses the patient-dependent electrical parameter, the current waveform also having a therapeutic discharge portion, with sufficient energy for performing therapy, having an initial discharge current controlled by the control circuit based on the patient-dependent electrical parameter as sensed by the sensor, the sensing pulse portion having a discharge current that is at least about one-third of the initial discharge current of the therapeutic discharge portion.

2. The electrotherapy circuit of claim 1 wherein the patient-dependent electrical parameter comprises impedance of the patient.

3. The electrotherapy circuit of claim 1 wherein the sensing pulse portion has a discharge current that is at least about half the initial discharge current of the therapeutic discharge portion.

4. The electrotherapy circuit of claim 1 wherein the sensing pulse portion has a non-alternating discharge current.

5. The electrotherapy circuit of claim 1 further comprising a charging circuit for charging the charge storage device, wherein the discharge of the charge storage device occurs without recharging of the charge storage device between the sensing pulse portion and the therapeutic discharge portion of the current waveform.

6. The electrotherapy circuit of claim 1 wherein the control circuit controls discharge of the charge storage device through the electrodes, based on the patient-dependent electrical parameter as sensed by the sensor, in a manner so as to reduce dependence of peak discharge current on the patient-dependent electrical parameter during the therapeutic discharge portion of the current waveform.

7. The electrotherapy circuit of claim 6 wherein the patient-dependent electrical parameter comprises impedance of the patient, and the peak discharge current if the impedance of the patient is 15 ohms is no more than about twice the peak discharge current if the impedance of the patient is 125 ohms.

8. The electrotherapy circuit of claim 1 further comprising a variable impedance connected between the charge storage device and one of the electrodes, the control circuit being connected to the variable impedance and controlling discharge of the charge storage device by controlling the variable impedance during discharge of the charge storage device.

9. The electrotherapy circuit of claim 8 wherein the patient-dependent electrical parameter comprises impedance of the patient, and, during the therapeutic discharge portion of the discharge of the charge storage device, the control circuit selects the impedance of the variable impedance inversely with respect to the impedance of the patient as sensed by the sensor during the sensing pulse portion.

10. The electrotherapy circuit of claim 9 wherein the therapeutic discharge portion of the current waveform is rectilinear.

11. The electrotherapy circuit of claim 1 wherein the variable impedance comprises a variable resistive circuit.

12. The electrotherapy circuit of claim 11 wherein the resistive circuit comprises a plurality of discrete resistors.

13. The electrotherapy circuit of claim 12 further comprising a switching circuit connected to the plurality of resistors that selectively provides at least one path for flow of electric current from the charge storage device through a subset of the plurality of resistors to one of the discharge electrodes.

14. The electrotherapy circuit of claim 13 wherein the control circuit controls the switching circuit to select the subset of the resistors through which the electric current flows, the control circuit selecting different subsets of the resistors during different portions of discharge of the charge storage device so as to produce a rectilinear current waveform.

15. The electrotherapy circuit of claim 13 wherein the resistors are connected together in series.

16. The electrotherapy circuit of claim 15 wherein the switching circuit selectively provides the path for flow of electric current by shorting out resistors not in the subset through which the path extends.

17. The electrotherapy circuit of claim 12 wherein the resistors are stepped in a binary sequence.

18. The electrotherapy circuit of claim 1 wherein the sensor is a current sensor.

19. The electrotherapy circuit of claim 18 wherein the sensor is a current sense transformer.

20. The electrotherapy circuit of claim 1 further comprising at least one switch connected between the charge storage device and one of the electrodes that, when closed, creates a closed circuit for flow of current from the charge storage device to the electrodes.

21. The electrotherapy circuit of claim 20 wherein the at least one switch comprises a plurality of switches arranged as an H-bridge.

22. The electrotherapy circuit of claim 1 wherein the current waveform comprises a first phase and a second phase having a polarity opposite to the first phase.

23. The electrotherapy circuit of claim 1 wherein the control circuit comprises a microprocessor.

24. The electrotherapy circuit of claim 1 wherein the control circuit is hard-wired.

25. The electrotherapy circuit of claim 1 wherein the current waveform comprises a defibrillation pulse.

26. The electrotherapy circuit of claim 1 wherein the electrodes are non-implanted.

27. The electrotherapy circuit of claim 1 wherein the charge storage device comprises at least one capacitor.

28. The electrotherapy circuit of claim 27 wherein the charge storage device is a single capacitor.

29. A method of forming an electrotherapy current waveform, comprising the steps of:
   charging a charge storage device having opposite poles;
   discharging the charge storage device through at least two discharge electrodes connected by electrical circuitry to the opposite poles of the charge storage device, the discharge of the charge storage device having a sensing pulse portion having insufficient energy for performing therapy and a discharge portion having sufficient energy for performing therapy;
   sensing a patient-dependent electrical parameter during the sensing pulse portion of the discharge of the charge storage device; and
   controlling an initial discharge current of the therapeutic discharge portion of the discharge of the charge storage device, based on the sensed patient-dependent electrical parameter,
   the sensing pulse portion having a discharge current that is at least about one-third the initial discharge current of the therapeutic discharge portion.

30. The method of claim 29 wherein the patient-dependent electrical parameter comprises impedance of the patient.

31. The method of claim 29 wherein the sensing pulse portion has a discharge current that is at least about half the initial discharge current of the therapeutic discharge portion.

32. The method of claim 29 wherein the sensing pulse portion has a non-alternating discharge current.

33. The method of claim 29 wherein the step of discharging the charge storage device is performed without recharging the charge storage device between the sensing pulse portion and the therapeutic discharge portion of the current waveform.

34. The method of claim 29 wherein the step of controlling discharge of the charge storage device through the electrodes, based on the sensed patient-dependent electrical parameter, comprises reducing dependence of peak discharge current on the electrical parameter during the therapeutic discharge portion of the current waveform.

35. The method of claim 34 wherein the patient-dependent electrical parameter comprises impedance of the patient, and the peak discharge current if the impedance of the patient is 15 ohms is no more than about twice the peak discharge current if the impedance of the patient is 125 ohms.

36. The method of claim 29 wherein:
   the step of discharging the storage device comprises discharging through a variable impedance connected between the charge storage device and one of the electrodes; and
   the step of controlling discharge of the charge storage device comprises controlling the variable impedance during discharge of the charge storage device based on the sensed patient-dependent electrical parameter.

37. The method of claim 36 wherein the patient-dependent electrical parameter comprises impedance of the patient, and the step of controlling the variable impedance comprises, during the therapeutic discharge portion, setting the variable impedance inversely with respect to the impedance of the patient as sensed during the sensing pulse portion.

38. The method of claim 36 wherein the variable impedance comprises a plurality of discrete resistors and the step of controlling the variable impedance comprises selectively providing at least one path for flow of electric current from the charge storage device through a subset of the plurality of resistors to one of the discharge electrodes.

39. The method of claim 38 wherein the step of providing the path for flow of electric current comprises selecting different subsets of the resistors during different portions of discharge of the charge storage device so as to produce a rectilinear current waveform.

40. The method of claim 38 wherein the resistors are connected together in series and the step of providing the path for flow of electric current comprises shorting out resistors not in the subset through which the path extends.

41. The method of claim 29 wherein the current waveform comprises a first phase and a second phase, the second phase having a polarity opposite to the first phase.

42. The method of claim 29 wherein the current waveform comprises a defibrillation pulse.

43. The method of claim 29 further comprising the step of applying the electrodes externally to the patient prior to discharging the charge storage device.

44. The method of claim 43 wherein the electrodes are applied directly to the patient's heart during surgery.

45. A method of forming an electrotherapy current waveform, comprising the steps of:
   charging a charge storage device having opposite poles;
   discharging the charge storage device through at least two discharge electrodes connected by electrical circuitry to the opposite poles of the charge storage device, the discharge of the charge storage device having a sensing pulse portion having insufficient energy for performing therapy and a discharge portion having sufficient energy for performing therapy;
   sensing a patient-dependent electrical parameter during the sensing pulse portion of the discharge of the charge storage device; and
   controlling an initial discharge current of the therapeutic discharge portion of the discharge of the charge storage device, based on the sensed patient-dependent electrical parameter;
   the sensing pulse portion of the current waveform being integral with the therapeutic discharge portion of the current waveform.

46. The method of claim 45 wherein the step of discharging the charge storage device comprises applying the current waveform as a defibrillation pulse to a patient.

47. The method of claim 45 wherein the step of discharging the charge storage device comprises applying the current waveform transthoracically to a patient.

48. The method of claim 45 wherein the therapeutic discharge portion comprises a phase having a ripple.

49. The method of claim 45 wherein the ripple has more than two teeth.

50. The method of claim 45 wherein the therapeutic discharge portion includes one phase followed by another phase having a polarity opposite that of the one phase.

51. The method of claim 50 wherein the other phase has a duration less than that of the one phase.

52. The method of claim 45 wherein the charge storage device is located externally of a patient's body through which the charge storage device is discharged during the discharging step.

53. An electrotherapy circuit for administering to a patient a current waveform, comprising:

a charge storage device having opposite poles;

at least two discharge electrodes connected by electrical circuitry to the opposite poles of the charge storage device;

a sensor that senses a patient-dependent electrical parameter during a sensing pulse portion of a current waveform, the sensing pulse portion having insufficient energy for performing therapy; and a control circuit, connected to the sensor and the charge storage device, for controlling discharge of the charge storage device through the electrodes, the discharge of the charge storage device comprising the current waveform having the sensing pulse portion during which the sensor senses a patient-dependent electrical parameter, the current waveform also having a therapeutic discharge portion, with sufficient energy for performing therapy, having an initial discharge current controlled by the control circuit based on the patient-dependent electrical parameter as sensed by the sensor, the sensing pulse portion of the current waveform being integral with the therapeutic discharge portion of the current waveform.

* * * * *